United States Patent

Novotny et al.

[11] Patent Number: 5,110,429
[45] Date of Patent: May 5, 1992

[54] METHOD AND ARRANGEMENT FOR DIAGNOSTICS OF FRICTION SYSTEMS OF MOTORS

[75] Inventors: Ladislav Novotny; Robert Kalvoda, both of Prague; Vladimir Novák; Karel Uher, both of Doksy, all of Czechoslovakia

[73] Assignee: JZD Valassko Se Sidlem Ve Vlachovicich, Gottwaldov, Czechoslovakia

[21] Appl. No.: 458,918

[22] Filed: Dec. 29, 1989

[30] Foreign Application Priority Data

Dec. 30, 1988 [CS] Czechoslovakia ............... 9111-88
Dec. 30, 1988 [CS] Czechoslovakia ............... 9113-88

[51] Int. Cl.$^5$ ................................................ C25F 7/00
[52] U.S. Cl. ................................... 204/153.1; 73/53.07
[58] Field of Search .................. 204/413, 153.1, 434; 73/64

[56] References Cited

U.S. PATENT DOCUMENTS

| | | | |
|---|---|---|---|
| 4,029,554 | 6/1977 | Ellison | 204/153.1 |
| 4,448,887 | 5/1984 | Kauffman et al. | 73/64 |
| 4,497,200 | 2/1985 | Tournier | 73/64 |
| 4,646,070 | 2/1987 | Yasuhara et al. | 73/64 |
| 4,764,258 | 8/1988 | Kauffman et al. | 204/153.1 |

Primary Examiner—John Niebling
Assistant Examiner—Bruce F. Bell

[57] ABSTRACT

A method for diagnosing friction systems involves the partial transfer of metallic microparticles dispersed in lubricant into a solution to be analyzed. The sample is turned alkaline, and after introduction of an electrode system, the dependence of current on an applied voltage in a given range of potentials is recorded. A determined amount of triethanolamine is added to the analyzed solution; the recording of current-voltage curve is repeated and from results of measurement the degree of wear and the technical state of the motor and of the used lubricant is estimated. The detection electrode in electrolysis is a droplet of mercury having an optimum radius between 0.05 and 0.4 mm, a renewed mercury meniscus electrode or a film mercury electrode. An exemplary apparatus for performing the method is disclosed.

6 Claims, 9 Drawing Sheets

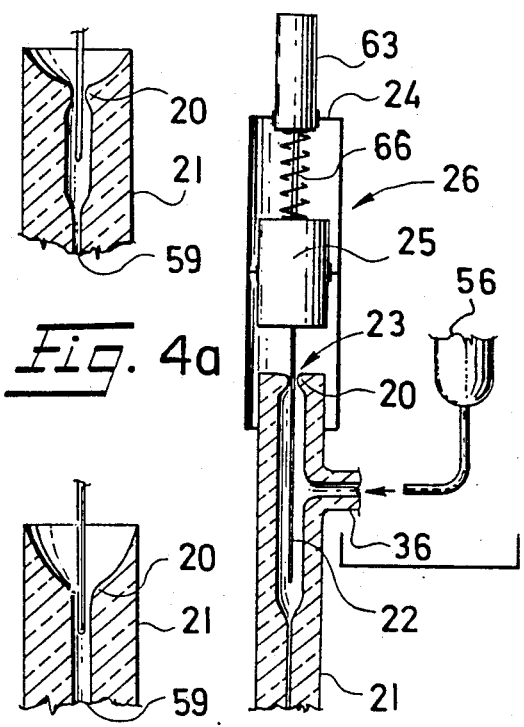
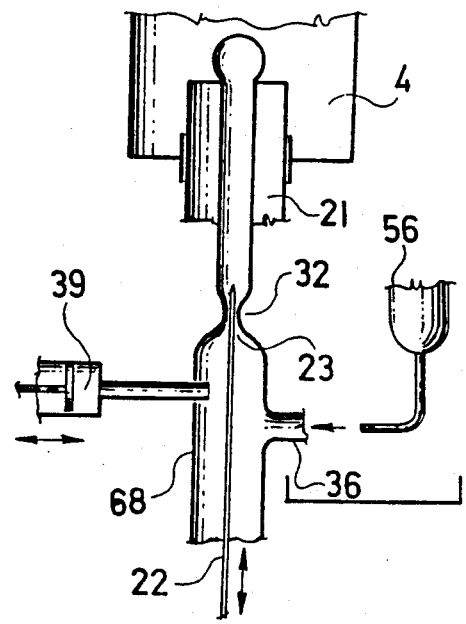
Fig. 4a
Fig. 4b
Fig. 4c
Fig. 5
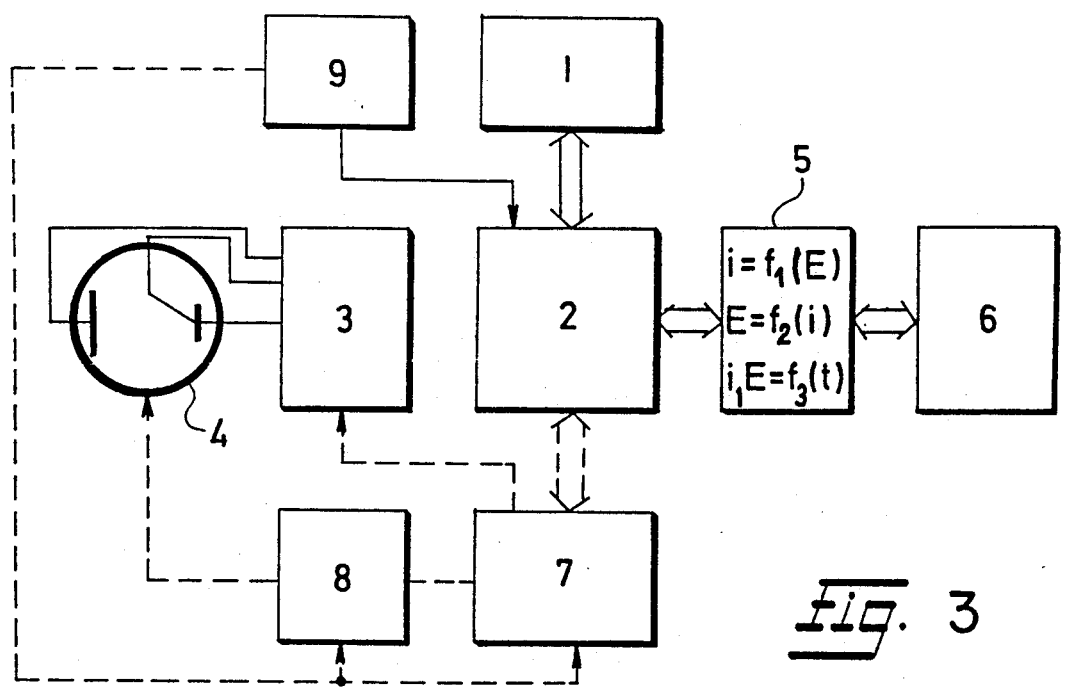
Fig. 3

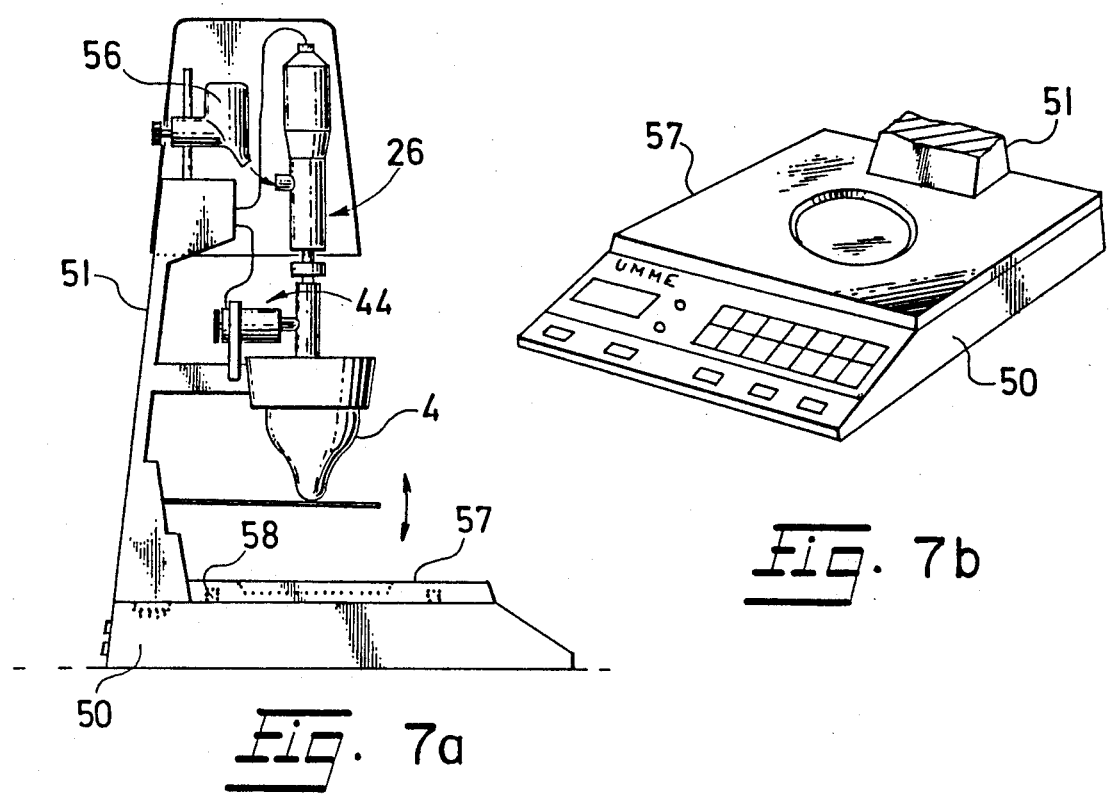
Fig. 7a
Fig. 7b
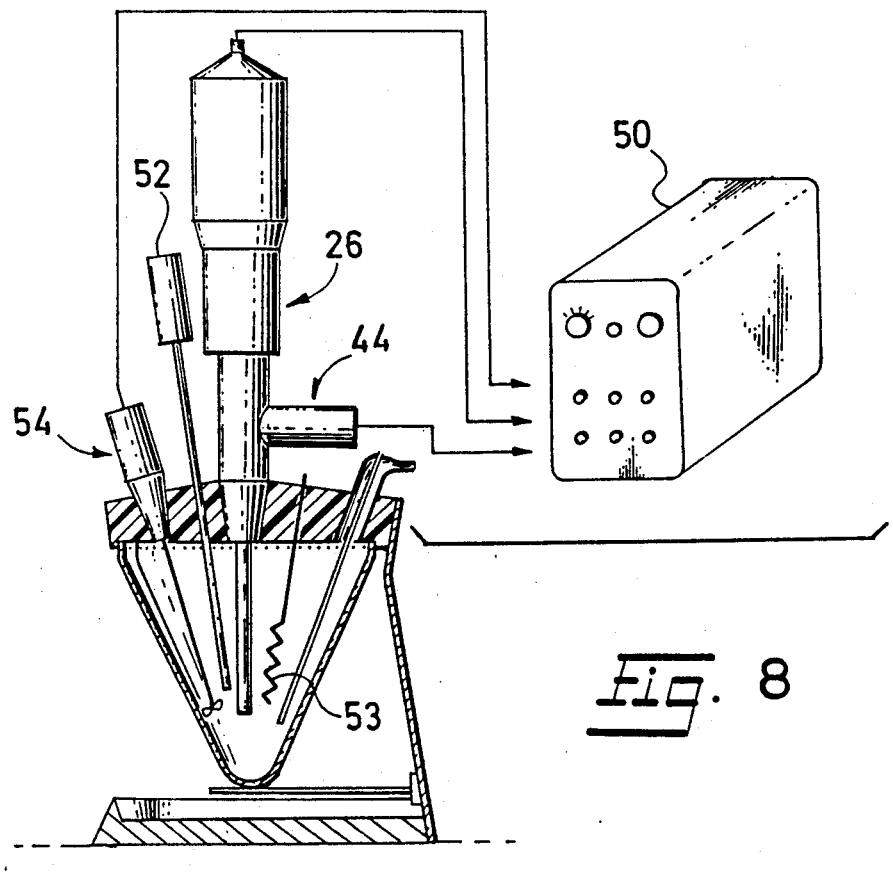
Fig. 8

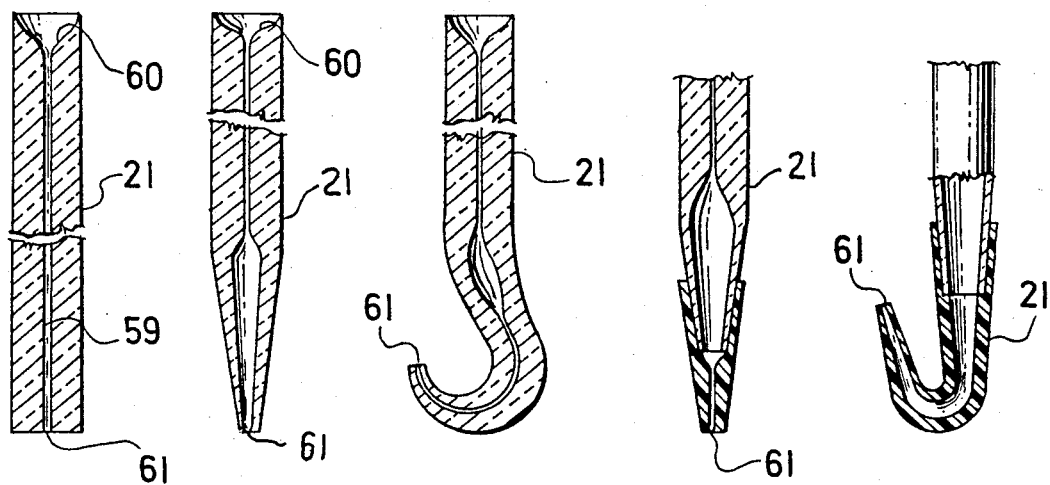
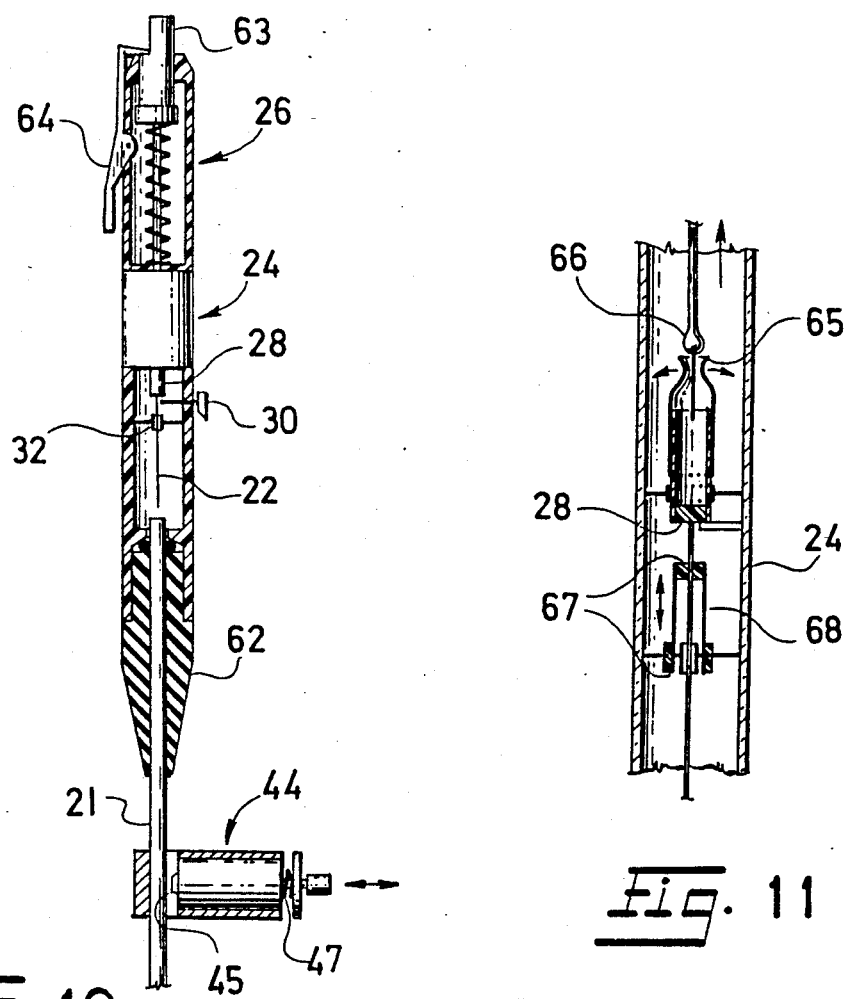

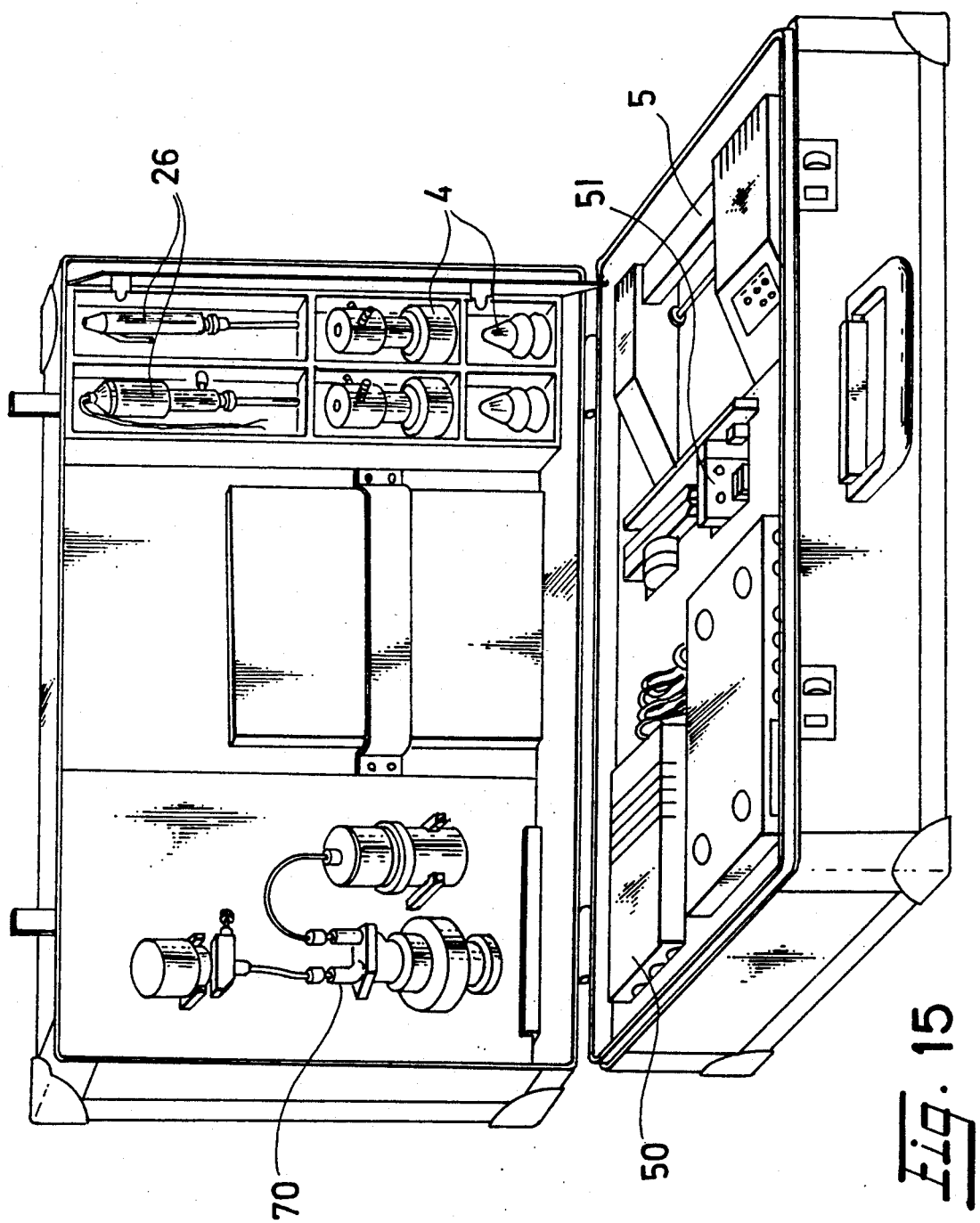

METHOD AND ARRANGEMENT FOR DIAGOSTICS OF FRICTION SYSTEMS OF MOTORS

FIELD OF THE INVENTION

This invention relates to the method and an apparatus for diagnosing friction systems of motors based on an analysis of unused and used lubricant.

BACKGROUND OF THE INVENTION

The analyses of used motor oils, especially by large-scale users of oil combustion engines, has been in practice for many years. See, Brown et al., *Particle Size Independent Spectometric Determination of Wear Metals in Aircraft Lubricating Oils*, 1980 Anal. Chem. 52, 2365-2370.

With the development of more efficient motors and better lubricants, some of the old-fashioned and inconvenient methods based on classical chemical analysis were abandoned. In recent years, the results of motor oil analysis began to be widely used for estimating and controlling the wear of motors and kinetic mechanisms. It is known that while the motor or the mechanism operates, it sheds microparticles of the metals of which the mechanism consists and these particles get transferred into the oil or the lubricant. By ascertaining the concentrations of individual metals in lubricant and the change in concentration over time, it is possible to estimate objectively the degree of wear and the technical state of the motor, to detect in time an imminent damage, etc., provided certain standard conditions for the analysis are maintained. See, generally, Eisenstraut et al., *Spectrometric Oil Analysis, Detecting Engine Failures Before They Occur*, 1984 Anal. Chem. 56, 1086-1094.

Two known methods for analyzing lubricants have proved best suited so far. See, Kauffman, et al., *Quantitative Multielement Determination of Metallic Wear Species in Lubricating Oils and Hydraulic Fluid*, 1982 Anal. Chem. 54, 975-979. These methods are atomic emission spectrography (AES) and atomic absorption flame spectrometry (AAS). Lately the AAS is the most preferred method. In the AAS method, the sample of oil after filtering and dilution by an appropriate solvent is burnt in a special burner while the absorption spectrum is measured by a highly sensitive apparatus.

In spite of high cost, operation complications, unfitness for current workshop conditions and other limitations (see below) the spectral tribodiagnostics is at present the most successful and widely applied method of objective triboanalysis, used especially in the USA, Canada and West Europe.

There do exist, however, other methods of technical diagnosis like the vibration and acoustic method and methods based on estimation of combustion products. Their main disadvantage is that they usually only indicate the critical states of the motors and are not sufficiently sensitive and exact.

One of the limitations and drawbacks of the above spectral tribodiagnostic methods is that the information they provide concerns the total concentration of the elements and not the form in which they occur, for example their oxidation states. They do not allow determination of organic components of the samples or detection of changes in lubricants. For some non-primary metals, e.g. lead, their sensitivity is limited. Their direct applicability for analysis of dispersed abraded particles larger than 10 µm is also restricted or impossible. Their relatively high cost, restricted use in current workshop conditions, limited precision, bulkiness, etc. make these methods disadvantageous.

SUMMARY OF THE INVENTION

It is an object of the invention to overcome the above-mentioned drawbacks of the known methods for obtaining diagnostic information from motor oils.

It has been discovered that the diagnostic information obtained from AAS or AES and from a technical check-up of oil combustion engines is in agreement with the intensity and the changes of a current signal in the current-voltage dependence measured according to the inventive method under maintenance of certain experimental conditions.

In order to obtain accurate results from the inventive method, it is necessary to use an appropriate apparatus and to adhere to a strict working procedure in preparing the sample of the solution for analysis, in preparing a detection mercury electrode or microelectrode and in recording the current-voltage dependence or its function. Modern voltametric methods are used with advantage for this purpose. The utilization of small-size mercury electrodes, the so-called minielectrodes and microelectrodes, proved especially convenient from the point of view of economy of space and simplicity of service, as well for consistent results and advantageous electrochemical properties of the electrode.

The method involves partial transfer of metallic microparticles dispersed in the lubricant into the solution to be analyzed, then the sample is turned alkaline. After introduction of an electrode system, the dependence of current on applied voltage in a given range of potentials is recorded. Then a determined amount of triethanolamine is added to the analyzed solution. The recording of a current-voltage curve is repeated and from results of measurement, the degree of wear and the technical state of the motor and the used lubricant is estimated. The detection electrode in electrolysis is a droplet of mercury of optimum radius between 0.05 and 0.4 mm, a renewed mercury meniscus electrode or a film mercury electrode.

The method of diagnosis of motors according to the present invention considerably widens the scope of objective tests of the state of combustion engines and other motors in view of detection and timely repair of minor defects, timely planned major repairs and avoiding unexpected break-downs. Providing that the diagnostic system is manufactured with a high standard, new possibilities will open for repair and maintenance practice, as the financial accessibility of the present method is more than 10 times more favorable than the spectral methods.

BRIEF DESCRIPTION OF THE DRAWING

With these and other objects in view, which will become apparent in the following detailed description, the present invention, which is shown by example only, will be clearly understood in connection with the accompanying drawing, in which:

FIG. 3 is a clock diagram of the apparatus of the invention;

FIGS. 4a, 4b and 4c are schematic view of a measuring electrode in a capillary tube;

FIG. 5 is another view similar to FIG. 4;

FIG. 6a is an overall view of the apparatus;
FIG. 6b is an enlarged detail of FIG. 6a;
FIG. 7a is a side view of the overall apparatus;
FIG. 7b is an overall view of the electronics panel;
FIG. 8 is another schematic view of an embodiment of the apparatus;
FIGS. 9a, 9b, 9c, 9d and 9e show several different embodiments of capillary tubes;
FIG. 10 shows a capillary tube and electrode and mercury drop dislodging device;
FIG. 11 is another schematic view of a measuring electrode;
FIG. 15 is a view of the invention in a portable kit form.

DESCRIPTION OF THE PREFERRED EMBODIMENTS

Figure 1:
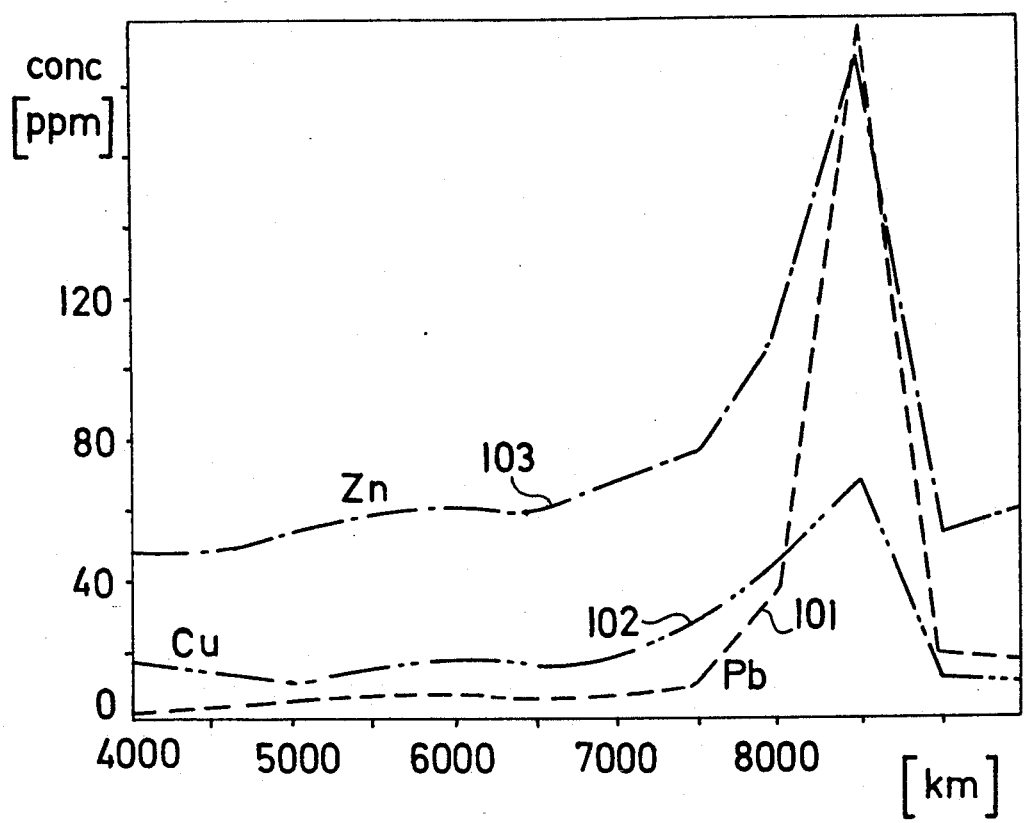
FIG. 1 is a graph of the dependence of copper, lead and zinc concentration in the extraction solution as a function of covered mileage.

The method of the invention is based on analysis of the used lubricant where the unused lubricant of given composition is introduced into the motor or is put into contact with it for a determined time. Then the motor is set for a certain time into motion whereupon a sample of the used lubricant is taken. The sample of the unused lubricant is brought into contact with an extraction solution of relative permittivity higher than 4 or at least partly transferred into the extraction solution. Then, into the extraction solution or into the sample of the unused lubricant a mercury-based measuring electrode, a reference electrode and, according to need, a given number of auxiliary electrodes are introduced.

By adjusting acidity and/or composition of the sample and applying electric voltage in a controlled manner between the measuring electrode, reference electrode and auxiliary electrodes, the intensity and course of electric current passing through the measuring electrode is followed, evaluated and recorded in dependence on the applied voltage.

Conclusions can be made from thus obtained data about the quality, composition and given physio-chemical properties of the unused lubricant or about the degree and form of its contamination. Then by taking the measuring, reference and auxiliary electrodes out of the extraction solution or the unused lubricant sample, by changing the sample of the unused lubricant for a sample of used lubricant and by repeating the described procedure, one can, on the basis of comparison with calibration data, determine the technical state of the motor, the localization and extent of its potential damage, and the functioning conditions of the motor.

According to a preferred embodiment, the used lubricant is tested with the extraction solution repeatedly in given time intervals whereby the intensity and/or the course of current passing through the measuring electrode in the extraction solution is measured after each interruption of contact of the used lubricant with the extraction solution. The concentrations of individual electrochemically active components, relative incidence of their oxidation states, concentration of compounds the absorption coefficient of which on the measuring electrode in the extracting solutions has a value higher than 100 m$^3$/mol, as well as concentration of polyaromatic substances are determined. The concentrations of these components is plotted (or compared) against the time of contact of the used lubricant with the diagnosed motor, the time of contact of the used lubricant with the extraction solution or parameters which are a function of these times.

The measuring electrodes is based on mercury, i.e. liquid mercury or mercury amalgam brought into a capillary orifice in the upper part of a measuring capillary and then in given intervals a constriction spike is alternately shifted in and out of the capillary orifice in such a way that within the selected mode of operation the flow of mercury into the measuring capillary is reduced, interrupted, renewed or changed in direction. After the mercury drop or the mercury menicus formed at the lower end of the measuring capillary reached the required shape, the motion of the constricting spike is stopped for a determined period after which the mercury drop or meniscus is removed and the whole sequence starting with the shift of the constricting spike is repeated.

Electric current is applied to the measuring electrode, a reference electrode and an auxiliary electrode dipping into the sample of extraction solution, while the value and/or time course of the electric potential of the measuring electrode is followed, evaluated and recorded, in dependence on the intensity and time course of the applied electric current.

The method of the invention is better understood by reference to the following two examples:

EXAMPLE 1

An example of application of the present invention is an estimation of the degree of wear of an oil combustion engine which is done as follows: From the lubrication system of the motor warmed-up to the usual operating temperature a sample of oil is taken. 5 g of this oil after addition of 3 ml of solvent based on chlorinated hydrocarbons is covered by 5 ml of hydrochloric acid diluted in proportion 2:1 and an extraction of the microparticles from oil into an aqueous solution is carried out for 15 minutes. Then, after addition of 45 ml of water, the extraction is continued for 10 more minutes. After separation of phases to 10 ml of aqueous phase, 5 ml of 6M potassium hydroxide are added. After dissolution of 2-3 g of sodium sulphite in the mixture, the resulting solution is placed in a cell and after connecting a source of linearly increasing voltage to the measuring mercury electrode and a reference silver chloride electrode, a current-voltage curve is recorded in the potential range $-0.24$ to $1.70$ V at the rate of voltage scan of 20 mV/sec. The measuring electrode is realized by a droplet of mercury having a radius about of about 0.3 mm formed in a given moment at the orifice of a special capillary by delivery of an appropriate micro-amount of mercury from a mercury reservoir. After recording of the above curve, 10 ml of 0.1 N triethanolamine are added to the solution in the cell and after the stirring, a current voltage curve is recorded in the range $-0.6$ to $-1.2$ V. From the course and comparison of both recordings, the concentration of copper, lead, zinc and iron in the motor oil is determined and by means of calibration data, the extent of wear of the friction system of the oil combustion engine is estimated.

The magnitudes of the measured signals or of the determined concentrations are plotted into graphs, e.g., as a function of mileage covered by the vehicle with the motor which is being followed. An increase of the measured signals or of the determined concentrations over certain level indicates the occurrence, the cause or even the possible location of a failure. FIG. 1 illustrates a graph of the dependence of copper curve 102, lead curve 101 and zinc curve 103 concentration in the extraction solution as a function of covered mileage. The exponential increase of concentration of these metals indicates wear of bearings. The position of maxima on the curves corresponds to the state of the motor before its breakdown, the steep decrease to the state after repair.

EXAMPLE 2

A sample of 5 g of used oil is taken from the lubricating system of the motor, after addition of 5 ml of a solvent based on chlorinated hydrocarbons, the solution is extracted for 5 minutes by 5 ml of 3M HCl and then a sample of 5 ml of aqueous extract is taken. Into this sample, sodium pyrophosphate and triethanolamine are added up to concentration of 0.1 mol/1. Then, the acidity of the sample is adjusted by addition of 1M NaOH to pH-9, whereupon the measuring electrode based on mercury drop and the silver chloride reference electrode are dipped into the sample of the extract. On the measuring electrode and reference electrode, voltage is applied linearly increasing form $-0.1$ to $-1.5$ V at the rate of 50 mV/s while a current-voltage curve is recorded. From the heights of peaks or waves formed in the region of $-0.3$ V and $-0.9$ V, the concentration of ions of iron in valency II and III is determined and from the data thus gained and compared with standard samples the abrasive properties of the metal present in the used oil can be determined as well as the total wear of the motor, the cylinder struts, the pistons, etc. The measured signals are plotted in graphs in dependence on covered mileage.

The apparatus of the invention is shown by way of example generally in FIGS. 2, 7, 8, and 15. FIG. 3 is a very basic block diagram of the method. A source of voltage 2 is adjusted by a setting program 1. Measuring electrodes 4 are connected with detection circuitry 3. Computational means 5 and recording or display means 6 are also provided. Means for dosing 8 and feeding 9 as well as sample treatment 7 are shown schematically in FIG. 3.

Figure 2:
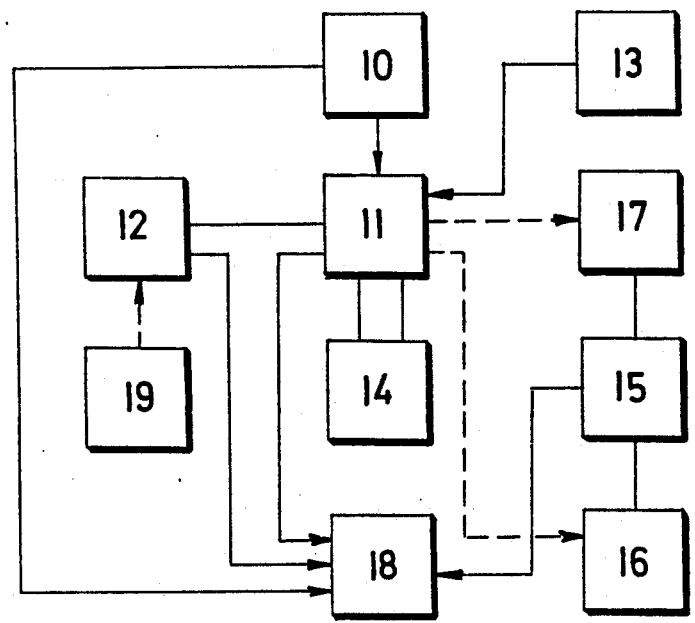
FIG. 2 is a block diagram of an electrode detector.

FIG. 2 shows one embodiment of detection circuitry (3 in FIG. 3). This embodiment includes setting means 10 for adjusting timing and control means 11 which is connected in parallel to a starting circuit 12, feeding circuit 13, memory 14 and electrodes 15, which may also be connected in parallel with other electro-mechanical mechanical accessories 16, spare voltage or current outputs 17 and a circuit of signals and control 18 which is also connected with the setting means 10. In certain cases the circuit for starting 12 can be connected to an external control means 19 as shown by the dotted line in FIG. 2.

The measuring electrode 26 is shown in greater detail in FIGS. 4 and 10. A capillary closure 20 of capillary 21 consists of constricting spike 22 the size and shape of which correspond to the size and shape of capillary orifice 23 of the capillary closure 20 or to the size and shape of at least a part of the inner space 59 of the capillary 21. In the upper part of the body of the measuring electrode 26 is a case 24 with a controlling mechanism 25.

The sliding segment 28 of the controlling mechanism 25 forms a component of the constricting spike 22 which passes through the closure 32 into the inner reservoir of mercury 29 (FIG. 6) and where the wall of the case 24 is provided by a lifting lever mechanism 30 with a lock 31.

The spike 22 (FIGS. 5, 6, and 10) is connected with the sliding segment 28 of the controlling mechanism 25 or is adjusted into its shape while at least in the passage through the closure 32, the difference between the outer diameter of the constricting spike 22 and the inner diameter of the closure 32 in less than 0.7 mm and the surface coarseness of the constricting spike 22 in the part passing through the closure 32 does not exceed 0.3 mm.

Figures 6A, 6B:
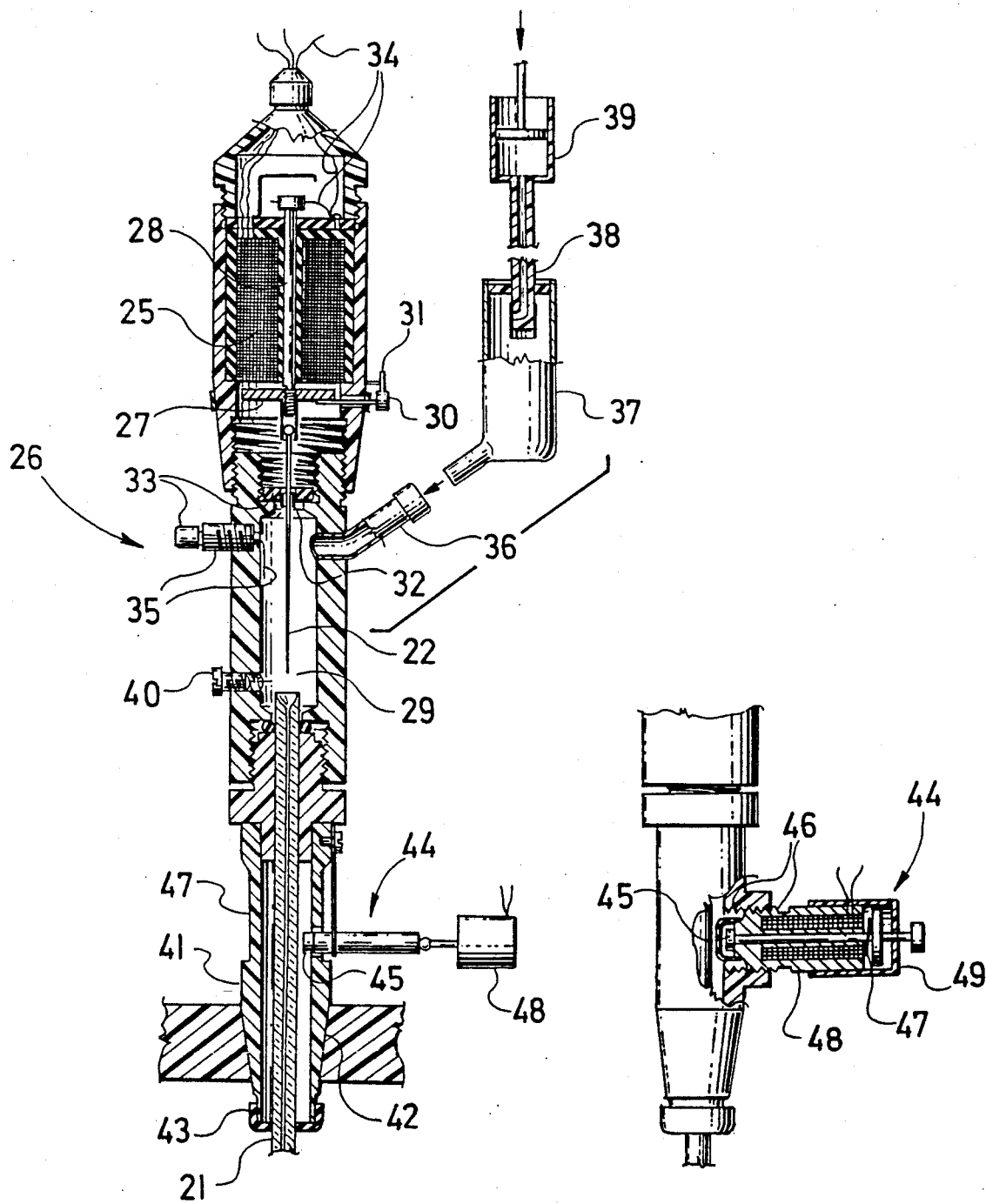

Referring to FIG. 6, the closure 32 is provided with packing 33. Electric contact 34 is made to the constricting spike 22 or the sliding segment 28 and an independent electric contact 35 is provided in the wall of the inner reservoir 29. An external reservoir 37 is connected to the inlet of mercury 36 and provided, according to need, with a valve 38 or overpressure doser 39.

Stop 40 is formed in the inner reservoir 29, and a reducing piece 41 at the lower part of the body of the measuring electrode 26 is shaped so as to fit input 42 in the bead or wall of the arrangement in which the electrode is held, while in the lower part of the reducing piece 41 the packing membrane 43 is fixed.

A mercury drop dislodging device 44 is attached to the reducing piece 41, to the body of the measuring electrode 26 or to the capillary wall 21, enabling adjustment of amplitude of hammer 45 and provided by the adjustable mechanism 46 which ca be shifted along the axis of the hammer 45, while the essential parts of the dislodging device 44 are hammer 45, elastic 47, and force element 48.

The setting means 10, timing and control means 11, starting means 12, memory 14, signals and control means 18 and, according to need, even the feeding unit 13, can be in the form of a screened and encased portable controlling block 50 (FIGS. 7 and 8) connected with the measuring electrode 26 through the drop dislodging device 44.

The entire apparatus can be composed of a disassemblable stand 51 with clamps adjusted for the body of the measuring electrode 26, for the reference electrode 52, for the auxiliary electrode 53, for the stirrer 54, for an inert gas doser 55, for external reservoir 56 and, according to need, for overpressure doser 39, for the measuring system 4, for waste pan 57 and stabilizing support 58.

Referring now to FIG. 9, a set of capillaries 21 have inner bore 59 in the upper part in the form of a funnel shaped saddle 60, and in the lower part there are, in a given sequence, sections of cylindrical, conically widening and conically narrowing diameters, down to the orifice 61. An evacuation arrangement has an adapter corresponding by its shape and size to the lower end of the capillary 21.

Referring now to FIG. 10, the penshaped body of the measuring electrode 26 consists of the electrode clamp 62 of the capillary 21 connected to the inner reservoir 29 with an independent electric contact 35, while above the inner reservoir 29 is mounted the control mechanism 25 for reproducible one way or periodic shifts of the constricting spike 22 coupled with the starting mechanism 63 shown as a push button, spring and limiting stop, and release 64.

Referring now to FIG. 11, the control mechanism 25 consists of a mechanical system such as sliding segment 28 with elastic neck 65, where rod 66 of the starting mechanism 63 is in the shape of a pointed cone of a fixing grip 67, and an elastic segment 68 and an adjustable stop 69.

Figure 12:
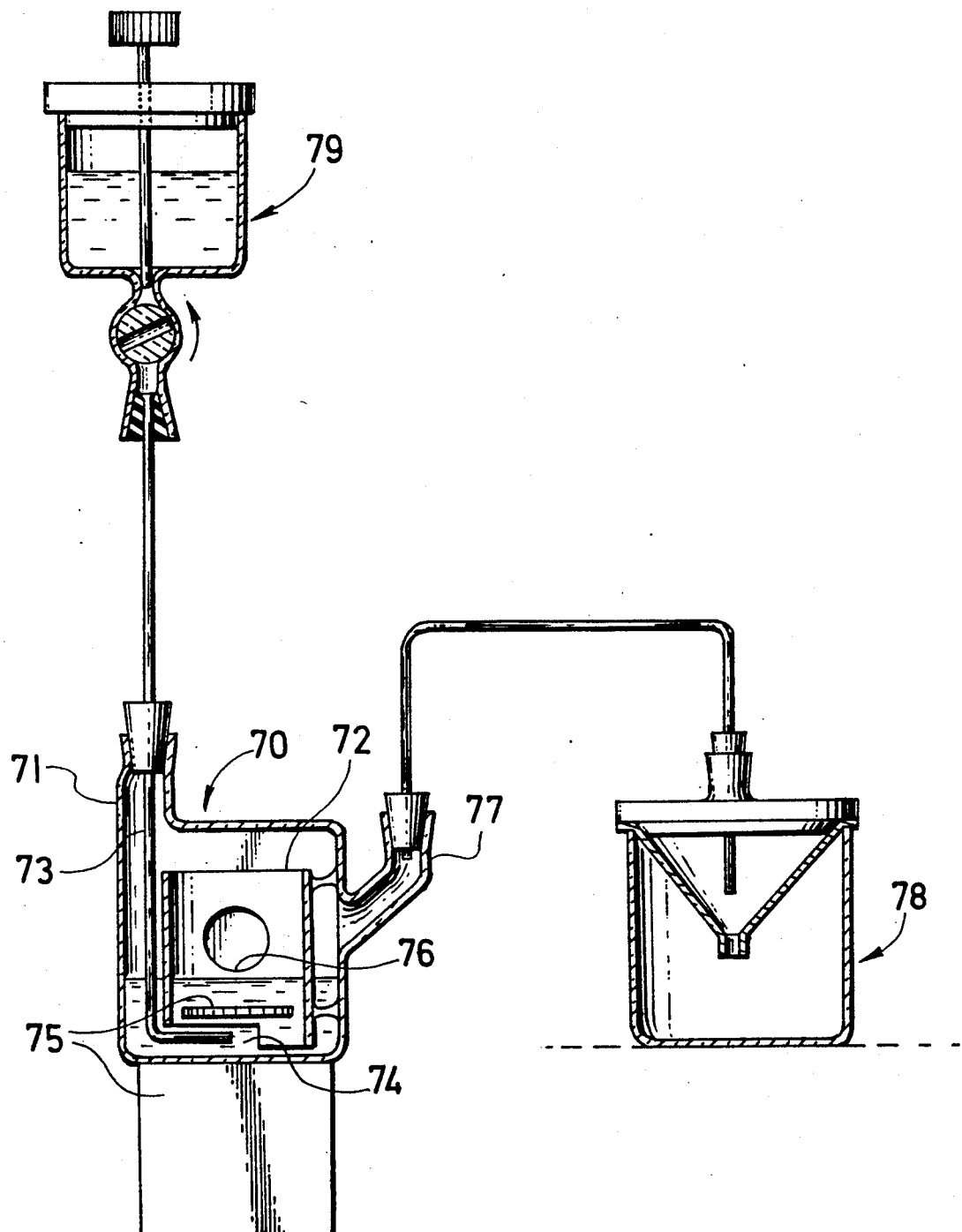
FIG. 12 is a schematic view of an extraction cell.

Referring now to FIG. 12, the extractor and/or sample treatment 7 contains an arrangement in which a closed extraction cell 70 is provided in its upper part near the wall by inlet neck 71 through which, between its wall and the shaped segment 72 fixed inside closed extraction cell 70, passes inlet tube 73 which ends near channel 74 close to the bottom of the closed extraction cell 70 near rotating stirrer 75, while in the wall of the shaped segment 72 is formed a slit 76. The outlet 77 from the side wall of the closed extraction cell 70 leads to collecting cell 78. Upper reservoir 79 is connected with the inlet neck 71 and the whole arrangement is supplemented, according to the need, by a mineralizing unit for chemical dissolution of the sample or for its incineration.

Figure 13:
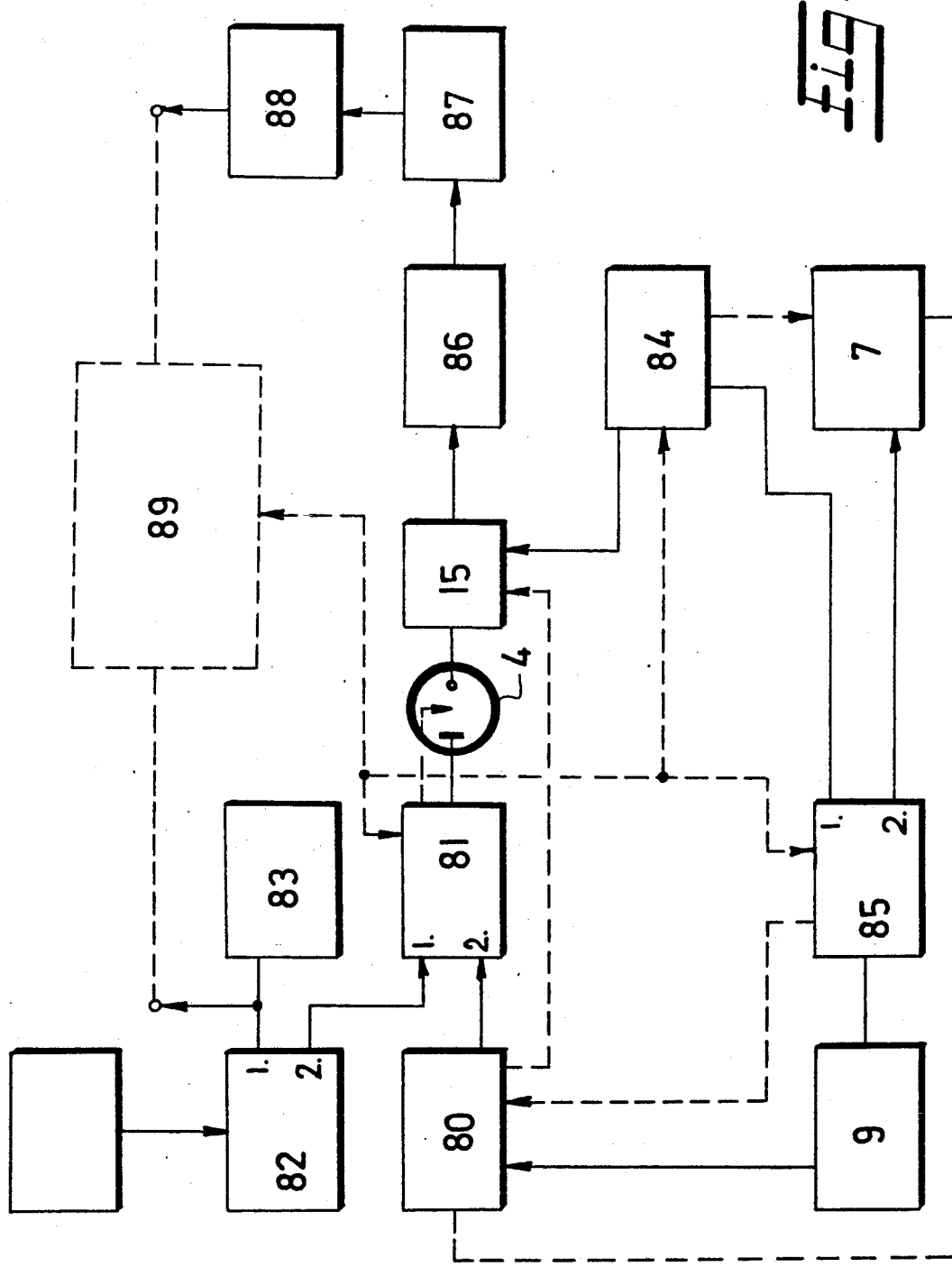
FIG. 13 is a block diagram of another embodiment of the apparatus.

Another example of a more detailed block scheme of the arrangement of the whole system is shown in FIG. 13 where the source of voltage 2 is formed by pulse generator 80, summator 81, scanning ramp 82 and voltmeter 83. The electrode detector 3 contains the electrodes 15, a clock of programmed electrode control 84 and a manual control 85. The sensing, processing and evaluating means 5 contains interface 86, memory 87 and amplifier and filter output 88. The recording, evaluation and control means 89 includes sensing, processing and evaluating means 5 and recording and display means 6, while in the given arrangement the output of the polarity and setting means 90 is connected with the scanning ramp 82 the first output of which is led to the input of the clock of voltmeter 83 and the second output to the first input of summator 81, while the outputs from the summator 81 are connected to the reference and auxiliary electrodes of the measuring system 4 into which dip in parallel the measuring sensor and the stirrer of the block of electrodes 15, the output of which is led to the input of interface 86, connected further to the input of memory 87 the output of which si led to the input of the amplifier and filter output 88 while the second input of the summator 81 is joined with the output of timing pulses 80, its input connected with the output of the feeding means 9, interconnected further with the manual control 85 the first output of which is joined with the input of the programmed electrode control 84 led to the input of the electrodes 15, and where the second output of the manual control 85 is connected to the extractor and/or sample treatment means 7.

Figure 14:
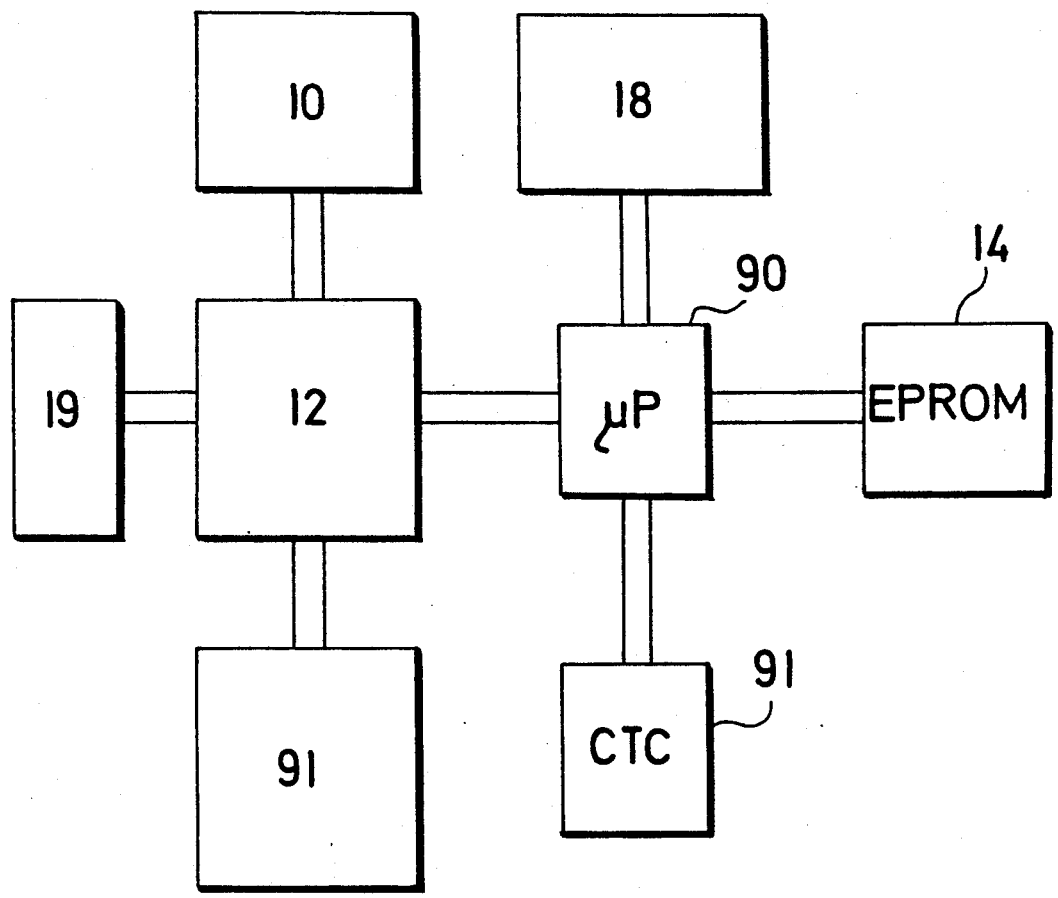
FIG. 14 is a block diagram of the apparatus using a microprocessor.

FIG. 14 shows another embodiment of the electrode detector 3 where the timing and control means 11 contains microprocessor 90 and program generator of time pulses 91 while the external control 19 is connected with the starting means 12 which is connected to the microprocessor 90 and the memory 14 and where the starting means 12 is independently connected to the setting means 10 such as a keyboard and to the electrodes 15. The microprocessor 90 is connected to signals and control means 18, and, in parallel, to the program generator of time pulses 91. The signals and control means 18 consists in that case of an optical part and an acoustic part and the external control 19 contains an electronic pulse system started automatically or by a mechanical impulse.

Although the invention is described and illustrated with reference to a plurality of embodiments thereof, it is to be expressly understood that it is in no way limited to the disclosure of such preferred embodiments but is capable of numerous modifications within the scope of the appended claims.

What we claim is:

1. A method for diagnosing friction systems by analyzing lubricant used in said systems, comprising the steps of
    taking a sample of used lubricant and transferring metallic microparticles dispersed in the sample into a solution to be analyzed;
    turning the solution alkaline;
    introducing a pair of electrodes into the solution;
    applying a series of voltages across the electrodes in steps;
    for each voltage applied across the electrodes, measuring the current passing through the electrodes;
    recording voltage and current coordinates;
    adding a predetermined amount of triethanolamine to the solution;
    repeating the steps of applying voltage and recording current-voltage coordinates;
    comparing the recorded coordinates to estimate the concentration of metallic microparticles in the solution.

2. A method as claimed in claim 1 wherein the solution to be analyzed has a permittivity of more than 4.

3. A method as claimed in claim 1 further comprising
    taking a sample of unused lubricant and repeating the steps as with the used lubricant; and
    comparing the results obtained with used and unused lubricant.

4. A method as claimed in claim 1 wherein the step of transferring metallic microparticles dispersed in the sample into a solution to be analyzed is performed by
    the addition of a solvent based on chlorinated hydrocarbons and the addition of a solution of HCL.

5. A method as claimed in claim 1 wherein the step of applying a series of voltages across the electrodes in steps comprises
    applying a first voltage of from $-0.1$ to $-0.24$ volts and increasing said voltage in steps at a rate of from 20 mV to 50 mV per second up to a final voltage of from $-0.9$ V to $-1.70$ V.

6. A method as claimed in claim 1 wherein the predetermined amount of triethanolamine is 10 ml in concentration up to 0.1N.

* * * * *